US008864835B2

(12) United States Patent
Linares et al.

(10) Patent No.: US 8,864,835 B2
(45) Date of Patent: *Oct. 21, 2014

(54) MULTI-COMPONENT KNEE IMPLANT ASSEMBLY WITH MULTIPLE ARTICULATING AND TRAVELING SURFACES

(75) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 55 days.

This patent is subject to a terminal disclaimer.

(21) Appl. No.: 13/593,579

(22) Filed: Aug. 24, 2012

(65) Prior Publication Data
US 2013/0053972 A1    Feb. 28, 2013

Related U.S. Application Data

(60) Provisional application No. 61/526,708, filed on Aug. 24, 2011.

(51) Int. Cl.
*A61F 2/38*    (2006.01)
*A61F 2/30*    (2006.01)

(52) U.S. Cl.
CPC ........... *A61F 2/38* (2013.01); *A61F 2002/3895* (2013.01); *A61F 2002/30649* (2013.01)
USPC .................... 623/20.22; 623/20.14; 623/20.21

(58) Field of Classification Search
CPC ........ A61F 2/38; A61F 2/3854; A61F 2/3859
USPC ........ 606/88; 623/17.14, 19.12, 20.14, 20.15, 623/20.17, 20.19, 20.21, 20.2, 20.22, 20.23, 623/21.13, 21.16, 23.4

See application file for complete search history.

(56) References Cited

U.S. PATENT DOCUMENTS

| | | | |
|---|---|---|---|
| 1,051,444 | A | 1/1913 | Pleister |
| 2,314,445 | A | 3/1943 | DuVall |
| 2,667,644 | A | 2/1954 | Johnson |
| 2,821,979 | A | 2/1958 | Cameron |
| 3,694,820 | A | 10/1972 | Scales et al. |

(Continued)

FOREIGN PATENT DOCUMENTS

| | | |
|---|---|---|
| EP | 1228739 A2 | 8/2002 |
| WO | 9800076 A1 | 1/1998 |
| WO | 2004080331 A2 | 9/2004 |
| WO | 2009039164 A1 | 3/2009 |

OTHER PUBLICATIONS

Tan et al., "Developments of an Antimicrobial Microporous Polyurethane Membrane", Journal of Membrane Science, 289. 199-209 (2007).

*Primary Examiner* — Christopher D Prone
(74) *Attorney, Agent, or Firm* — Gifford, Krass, Sprinkle, Anderson & Citkowski, P.C.

(57) ABSTRACT

A multi-component joint assembly incorporated into reconditioned end surfaces established between an upper bone and an opposing lower bone. A first component is anchored into the upper reconditioned bone end surface and exhibits a first exposed support surface, a second component is anchored into the lower reconditioned bone end surface and exhibits a second exposed support surface. A spherical shaped and multi-directional supporting component is supported between the first and second anchored components.

5 Claims, 8 Drawing Sheets

(56) References Cited

U.S. PATENT DOCUMENTS

| | | | |
|---|---|---|---|
| 3,815,157 A | 6/1974 | Skorecki et al. | |
| 3,973,277 A | 8/1976 | Semple et al. | |
| 3,992,726 A * | 11/1976 | Freeman et al. | 623/23.4 |
| 4,040,131 A | 8/1977 | Gristina | |
| 4,045,825 A | 9/1977 | Stroot | |
| 4,483,023 A | 11/1984 | Hoffman, Jr. et al. | |
| 4,501,031 A | 2/1985 | McDaniel et al. | |
| 4,665,951 A | 5/1987 | Ellis | |
| 4,693,723 A | 9/1987 | Gabard | |
| 4,744,793 A | 5/1988 | Parr et al. | |
| 4,778,473 A | 10/1988 | Matthews et al. | |
| 4,792,336 A | 12/1988 | Hlavacek et al. | |
| 4,828,562 A | 5/1989 | Kenna | |
| 4,840,630 A | 6/1989 | Kitamura | |
| 4,851,005 A | 7/1989 | Hunt et al. | |
| 4,883,486 A | 11/1989 | Kapadia et al. | |
| 4,906,149 A | 3/1990 | Rockenfeller et al. | |
| 5,004,474 A | 4/1991 | Fronk et al. | |
| 5,078,745 A | 1/1992 | Rhenter et al. | |
| 5,171,325 A | 12/1992 | Aulie | |
| 5,263,984 A | 11/1993 | Li et al. | |
| 5,282,867 A | 2/1994 | Mikhail | |
| 5,376,119 A | 12/1994 | Zimmermann et al. | |
| 5,389,107 A | 2/1995 | Nassar et al. | |
| 5,413,604 A | 5/1995 | Hodge | |
| 5,417,693 A | 5/1995 | Sowden et al. | |
| 5,462,563 A | 10/1995 | Shearer et al. | |
| 5,480,443 A | 1/1996 | Elias | |
| 5,486,197 A | 1/1996 | Le et al. | |
| 5,507,819 A | 4/1996 | Wolf | |
| 5,554,194 A | 9/1996 | Sanders | |
| 5,571,191 A | 11/1996 | Fitz | |
| 5,575,819 A | 11/1996 | Amis et al. | |
| 5,593,448 A | 1/1997 | Dong | |
| 5,609,647 A | 3/1997 | Kalberer et al. | |
| 5,676,702 A | 10/1997 | Ratron et al. | |
| 5,702,469 A | 12/1997 | Whipple et al. | |
| 5,702,486 A | 12/1997 | Craig et al. | |
| 5,707,395 A | 1/1998 | Li | |
| 5,723,018 A | 3/1998 | Cyprien et al. | |
| 5,728,175 A | 3/1998 | Rincoe | |
| 5,741,335 A | 4/1998 | Gerber et al. | |
| 5,800,566 A | 9/1998 | Gramnas et al. | |
| 5,871,541 A | 2/1999 | Gerber | |
| 5,879,404 A | 3/1999 | Bateman et al. | |
| 5,921,358 A | 7/1999 | Gramnas et al. | |
| 5,961,555 A | 10/1999 | Huebner | |
| 6,001,106 A | 12/1999 | Ryan et al. | |
| 6,010,535 A | 1/2000 | Shah | |
| 6,117,175 A | 9/2000 | Bosredon | |
| 6,190,411 B1 | 2/2001 | Lo et al. | |
| 6,193,758 B1 | 2/2001 | Huebner | |
| 6,197,063 B1 | 3/2001 | Dews | |
| 6,245,109 B1 | 6/2001 | Mendes et al. | |
| 6,325,804 B1 | 12/2001 | Wenstrom, Jr. et al. | |
| 6,383,223 B1 | 5/2002 | Baehler et al. | |
| 6,582,715 B1 | 6/2003 | Barry et al. | |
| 6,620,197 B2 | 9/2003 | Maroney et al. | |
| 6,626,942 B1 | 9/2003 | Edberg et al. | |
| 6,645,251 B2 | 11/2003 | Salehi et al. | |
| 6,776,799 B2 | 8/2004 | Ball et al. | |
| 6,790,234 B1 | 9/2004 | Frankle | |
| 6,840,962 B1 | 1/2005 | Vacanti et al. | |
| 6,939,379 B2 | 9/2005 | Sklar | |
| 6,986,790 B2 | 1/2006 | Ball et al. | |
| 7,033,396 B2 | 4/2006 | Tornier | |
| 7,044,983 B1 | 5/2006 | Cheng et al. | |
| 7,056,340 B2 | 6/2006 | McKernan et al. | |
| 7,066,958 B2 | 6/2006 | Ferree | |
| 7,087,091 B1 | 8/2006 | Chen et al. | |
| 7,097,663 B1 | 8/2006 | Nicol et al. | |
| 7,101,398 B2 | 9/2006 | Dooris et al. | |
| 7,153,327 B1 | 12/2006 | Metzger | |
| 7,169,184 B2 | 1/2007 | Dalla Pria | |
| 7,175,663 B1 | 2/2007 | Stone | |
| 7,175,666 B2 | 2/2007 | Yao | |
| 7,189,261 B2 | 3/2007 | Dews et al. | |
| 7,309,360 B2 | 12/2007 | Tornier et al. | |
| 7,329,281 B2 | 2/2008 | Hays et al. | |
| 7,331,995 B2 | 2/2008 | Eisermann et al. | |
| 7,445,638 B2 | 11/2008 | Beguin et al. | |
| 7,462,197 B2 | 12/2008 | Tornier et al. | |
| 7,465,319 B2 | 12/2008 | Tornier | |
| 7,510,558 B2 | 3/2009 | Tallarida et al. | |
| 7,708,781 B2 | 5/2010 | Scheker | |
| 2001/0051831 A1 | 12/2001 | Subba Rao et al. | |
| 2002/0013627 A1 | 1/2002 | Geistlich et al. | |
| 2002/0143402 A1 | 10/2002 | Steinberg | |
| 2003/0130741 A1 | 7/2003 | McMinn | |
| 2004/0024460 A1 | 2/2004 | Ferree | |
| 2004/0064187 A1 | 4/2004 | Ball et al. | |
| 2004/0064188 A1 | 4/2004 | Ball et al. | |
| 2004/0210317 A1 | 10/2004 | Maroney et al. | |
| 2004/0225370 A1 | 11/2004 | Cruchet et al. | |
| 2004/0267370 A1 | 12/2004 | Ondrla | |
| 2005/0081867 A1 | 4/2005 | Murphy | |
| 2005/0187620 A1 | 8/2005 | Pai et al. | |
| 2005/0192674 A1 | 9/2005 | Ferree | |
| 2005/0261775 A1 | 11/2005 | Baum et al. | |
| 2005/0278032 A1 | 12/2005 | Tornier et al. | |
| 2006/0058886 A1 | 3/2006 | Wozencroft | |
| 2006/0074423 A1 | 4/2006 | Alleyne et al. | |
| 2006/0095132 A1 * | 5/2006 | Kirschman | 623/17.14 |
| 2006/0111787 A1 | 5/2006 | Bailie et al. | |
| 2006/0149370 A1 | 7/2006 | Schmieding et al. | |
| 2007/0005074 A1 | 1/2007 | Chudik | |
| 2007/0005137 A1 | 1/2007 | Kwak | |
| 2007/0054127 A1 * | 3/2007 | Hergenrother et al. | 428/411.1 |
| 2007/0088442 A1 | 4/2007 | Cima et al. | |
| 2008/0234830 A1 | 9/2008 | Hershberger et al. | |
| 2009/0039164 A1 | 2/2009 | Herwig et al. | |
| 2009/0088865 A1 | 4/2009 | Brehm | |
| 2009/0292364 A1 | 11/2009 | Linares | |
| 2010/0036499 A1 | 2/2010 | Pinskerova | |
| 2010/0191342 A1 | 7/2010 | Byrd et al. | |
| 2010/0305710 A1 | 12/2010 | Metzger et al. | |
| 2012/0029649 A1 | 2/2012 | Collazo et al. | |
| 2012/0136452 A1 | 5/2012 | Richter et al. | |
| 2012/0185054 A1 | 7/2012 | Maloney et al. | |

* cited by examiner

MULTI-COMPONENT KNEE IMPLANT ASSEMBLY WITH MULTIPLE ARTICULATING AND TRAVELING SURFACES

CROSS REFERENCE TO RELATED APPLICATIONS

The present application claims the priority of U.S. Ser. No. 61/526,708 filed Aug. 24, 2011.

BACKGROUND OF THE INVENTION

1. Field of the Invention

The present invention discloses an artificial joint assembly, such as is particularly configured for employing as a retrofit knee joint, and which combines multiple artificial components incorporated into first and second reconditioned joint defining surfaces for providing increased wear life in tandem with evenly distributed wear pattern/profile as well as enhanced flexibility and mobility.

2. Background of the Relevant Art

The prior art is well documented with examples of artificial knee implant assemblies. These include such as the spherical knee joint prosthesis of Bosredon, U.S. Pat. No. 6,117,175, the total knee implant of Byrd et al., US 2010/0191342 and the artificial implant component and method for securing disclosed in Elias, U.S. Pat. No. 5,480,443.

SUMMARY OF THE PRESENT INVENTION

The present invention discloses a multi-component joint assembly incorporated into reconditioned end surfaces established between an upper bone and an opposing lower bone. The assembly includes a first component anchored into the upper reconditioned bone end surface and exhibiting a first exposed support surface and second component anchored into the lower reconditioned bone end surface and exhibiting a second exposed support surface. A spherical shaped component is supported in at least one of eccentric rotational and linear/arcuate translatable fashion between the first and second anchored components.

Additional features include at least one of said components further exhibiting an arcuate and optionally inwardly flared track support surface. At least one of the components further exhibits a hemispherical recess for substantially seating the spherical shaped component. Other features of the joint assembly include each of the first, second and spherical shaped components further being constructed of at least one of a metal, plastic, polymer or composite material.

In other applications, a first pair of components are arranged at a first side of the assembly, with a second identical pair arranged at an opposite second side, such as is typical of a retrofit knee joint assembly. In this fashion, a subset pair of these components may further be employed in a ½ implant assembly associated with a selected side of the joint defining bones.

Other features include the spherical shaped component further exhibiting a multi-layer composition including a softer outer layer and at least one harder interior layer which can further include first and second inner layers establishing an eccentric rotational interface therebetween.

A plurality of surface projecting bearings are mounted within an innermost spherical shaped portion of the spherical component, these facilitating the eccentric rotational interface. A grid pattern of lubricating grooves defined in a surface of an innermost spherical shaped portion of said spherical component facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit knee joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's knee assembly (between the lower end of the upper femur bone and corresponding upper end of the lower tibia bone), however it is further understood that certain applications could in theory include other joint applications, either human or other mammalian. For purposes of ease and clarify of illustration, the various embodiments depicted further do not include reference to additional necessary components of the knee joints, such as including the patella (knee cap) and associated muscles, tendons and ligaments, the inclusion of which are assumed and which collectively define a functioning knee joint.

Figure 1:
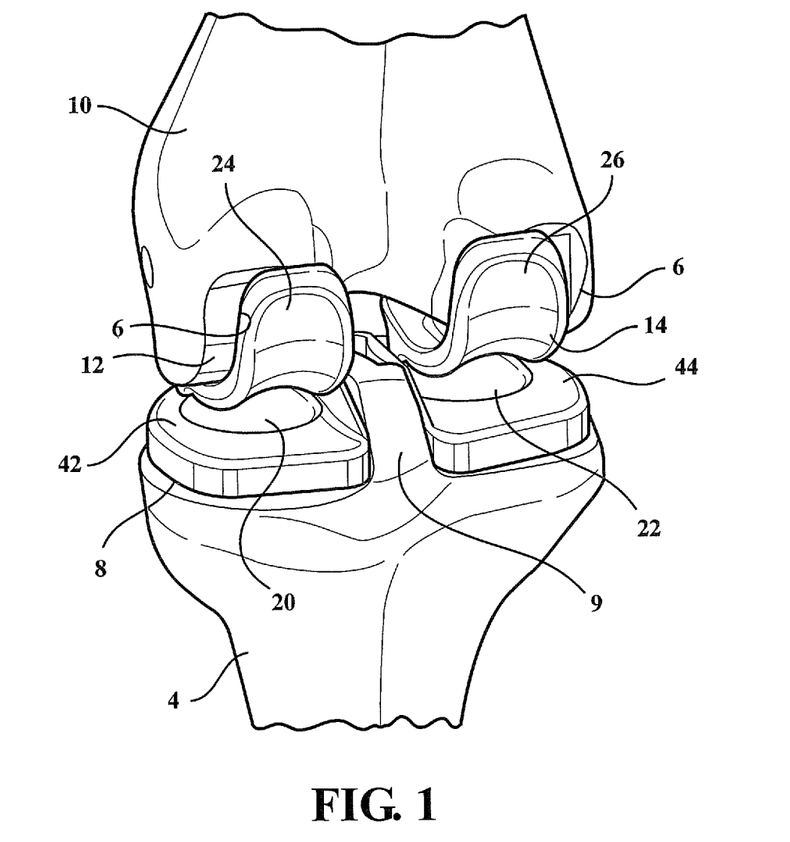
FIG. 1 is a perspective view of a knee implant assembly according to a first embodiment of the invention.

Referring now to FIG. 1, a perspective view is generally shown at 10 of a knee implant assembly according to a first embodiment of the invention and which is incorporated between an upper leg (femur) bone 2 and a lower leg (tibia) bone 4 (and with which an associated fibula bone is also not depicted). The present invention contemplates such as in situ reconditioning of the bone ends, illustrated by conditioned end profiles 6 configured into the bottom most end surface of the femur 2, as well as opposing upper end facing and recessed profiles 8 defined in the upper most end of tibia 4 with additional bridging location 9 defined between the substantially hemispherical shaped recessed profiles 8, Such reconditioning occurs following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Figure 8:
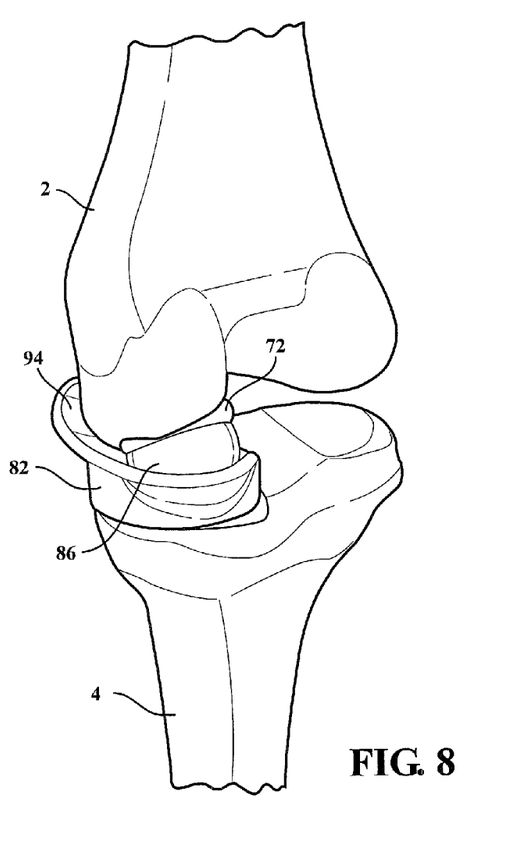
FIG. 8 is an illustration substantially identical to that previously depicted in FIG. 5 and presenting only a selected side or ½ implant assembly according to a further potential sub-variant.

Although not shown, such reconditioning can be employed with minimal interference to such necessary additional elements of the joint including each of the patella or knee cap, ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial (as depicted in FIG. 8) manner concurrent with any necessary degree of refashioning or removal of damaged bone or joint.

Figure 2:
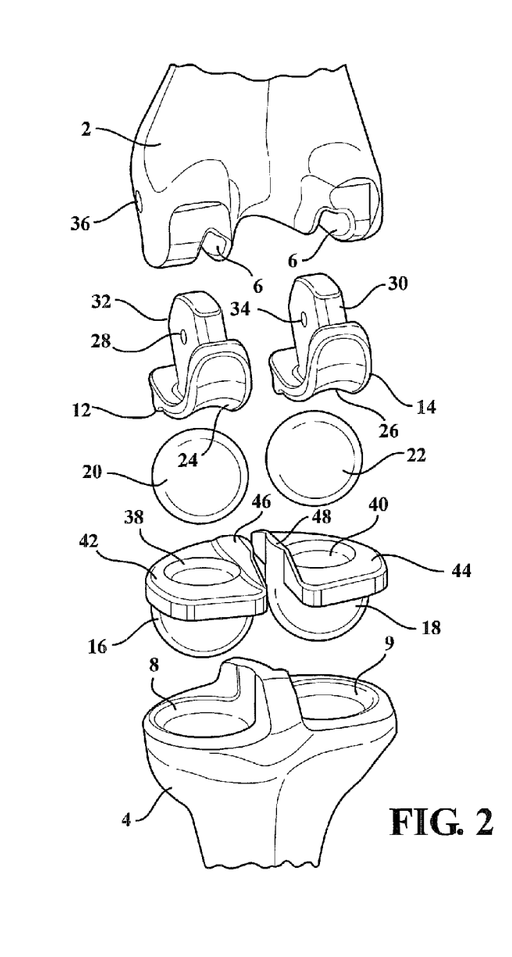
FIG. 2 is an exploded view of the multi-component assembly of FIG. 1 and better illustrating the reconditioned end-configurations established between the upper femur and lower tibia leg bones combined with the pairs of upper bone secured arcuate tracks, lower bone secured receiving troughs and intermediate positioned spherical inter-movable supports.

Referring to FIG. 1 again in collaboration with exploded view of FIG. 2, the multi-component assembly 10 better illustrates the reconditioned end-configurations 6 and 8 established between the upper femur 2 and lower tibia 4 leg bones combined with pairs of upper bone secured arcuate tracks 12 and 14, lower bone secured receiving troughs 16 and 18 (see as best shown in FIG. 2) and intermediate positioned spherical inter-movable supports 20 and 22. For purposes of the present description, a pair of implant components can also refer to a subset of upper and lower bone engaging implants as depicted in side-by-side fashion in FIG. 1 as well as ½ retrofit installed fashion as depicted in FIG. 8.

Each of the components a12-22 are constructed of any arrangement of metal, polymer, plastic, composite or other suitable material, with it further being understood that the individual pairs of components can be arrayed with any pattern of alternating materials, such that the outer (upper and lower affixed) pairs of components 12 & 14 and 16 & 18 can be constructed of a first material, with the intermediate positioned spherical (bearing) supports 20 and 22 being of a second material. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

Both the upper bone secured tracks 12 and 14 and lower bone secured troughs 16 and 18 are anchored in seating fashion within the inner recessed profiles 6 and 8 of the femur 2 and tibia 4 bones by use of a suitable medical cement (it further being understood that suitable bone adhesion can also be assisted or promoted by inner marrow in given circumstances). The upper tracks 12 and 14 each exhibit and arcuate, inwardly flared exposed surface (see at 24 and 26 in FIG. 2), with inner (reverse side) extending stems 28 and 30 recess mounting within mating recess configurations defined in the joint end defining face of the upper femur bone 2. Width extending apertures 32 and 34 defined in the stems 28 and 30 can also receive widthwise inserting pins 35 (again FIG. 2) extending through mating and aligning apertures formed widthwise through the femur bone 2 (see further at 36).

The lower bone secured inserts exhibiting seating troughs 16 and 18 each further include a generally semi-spherical shaped body with bottom convex surfaces which seat within the mating three dimensional recess profiles 8 established within the joint end face defining profiles of the lower tibia 4. The lower troughs 16 and 18 in turn exhibit upwardly facing and substantially semi-spherical inner recess 38 and 40 surrounded by upper lip or rim annular supporting edges 42 and 44. Inner opposing edge profiles of the troughs 16 and 18 are further defined by upward raised projections exhibiting inner opposing edges 46 and 48 which seat against the raised bridge location 9 defined in a mid location of the tibia end face again in the manner depicted in the assembled view of FIG. 1.

The spherical shaped supports 20 and 22 are dimensioned so that they substantially seat within the inner recesses 38 and 40 (see again FIG. 1) upon being fully installed in the manner depicted in FIG. 1. In this fashion, the spherical supports 20 and 22 establish rotatable eccentric support within the lower troughs 16 and 18 (in additional to a determined minor degree of side-to-side and/or fore-to-aft translation of the supports 20 and 22 within the troughs, such as due to designed tolerances within the recessed semi-spherical profiles 8) combined with the inwardly flared and arcuate surfaces 24 and 26 of the upper arcuate tracks 12 and 14 (these being again exposed following anchoring of the tracks within the femur end surface) establishing like rotational support against upper corresponding edges of the spherical supports 20 and 22 combined with longitudinal/arcuate (fore and aft) support. In this fashion, the joint assembly distributes motion along two interfaces (between upper bone anchored tracks 12 and 14 and intermediate spherical bearing supports 20 and 22, as well as separately between the bearing supports 20 and 22 and the lower tibia anchored troughs 16 and 18).

This arrangement further enables the upper interface between the tracks 12 and 14 and spherical bearings 20 and 22 to permit the bearings to translate along the arcuate paths 24 and 26 defined in the upper tracks 12 and 14, concurrent with its rotation at both the upper tracks and lower trough 16 and 18 interfaces, such as occurring during bending motion of the knee. As again previously indicated, additional configurations of muscles, ligaments, tendons and patella (knee cap) are provided and can include both natural (pre-existing) and/or synthetic materials, such as which are concurrently implanted or reconstructed in order to provide a dynamic and long-term implantable assembly.

Figure 3:
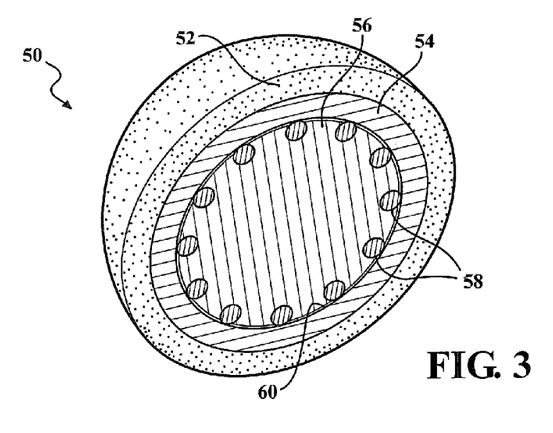
FIG. 3 is a cutaway view of a selected spherical inter-movable support and which illustrates its multi-material construction with softer outermost material, an intermediate harder material, and an innermost harder materials, an eccentric rotatable interface established between said intermediate and innermost layers further incorporating encapsulated ball bearings.

Referring now to FIG. 3, a cutaway view is generally shown at 50 of a selected spherical inter-movable support, such as again represented by each of 20 and 22 in FIGS. 1 and 2. The cutaway view of FIG. 3 illustrates one non-limiting example of a multi-layer material construction and which includes a softer (typically plastic or plastic composite) outermost material layer 52, an intermediate harder 54 material (typically another plastic), and an innermost harder material 56 (which can be of a similar hardness as the intermediate layer 54 as well as relatively harder or softer based on the preferences of the application).

Figure 4:
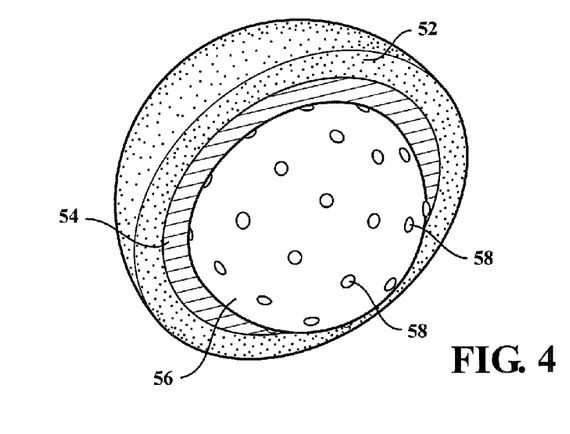
FIG. 4 is an illustration similar to FIG. 3 and depicting the outermost and intermediate layers of the spherical support again in cutaway fashion, along with the innermost portion exhibited in three dimension perspective with surface supported bearings.

An eccentric rotatable interface is established between the intermediate 54 and innermost 56 layers, and which further includes a plurality of ball bearings 58 encapsulated within the inner most layer 56 with arcuate edge portions thereof projecting from the spherical surface thereof (see further in FIG. 4 which depicts the same variant with the exception that the innermost material 56 is depicted in three dimension relative to the outer planar cutaway layers). In this fashion, an inner encapsulated and rotational interface 60 established between an inner-most spherical body defined by the innermost layer 56 and its edge projecting and individually eccentric mounted bearings 58 and the opposing inwardly facing boundary of the intermediate layer 54 provides an additional measure of dynamic compress and multi-axial eccentric motion to complement the performance of such as the non-limiting joint application of FIGS. 1 and 2.

Figure 5:
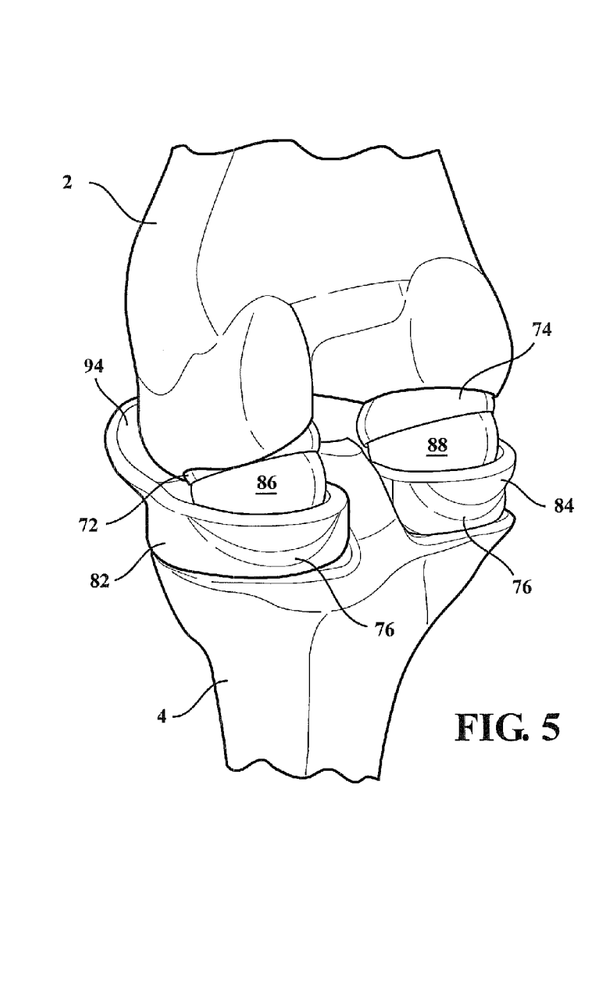
FIG. 5 is an illustration similar to FIG. 1 of a knee implant assembly according to a further preferred variant.
Figure 6:
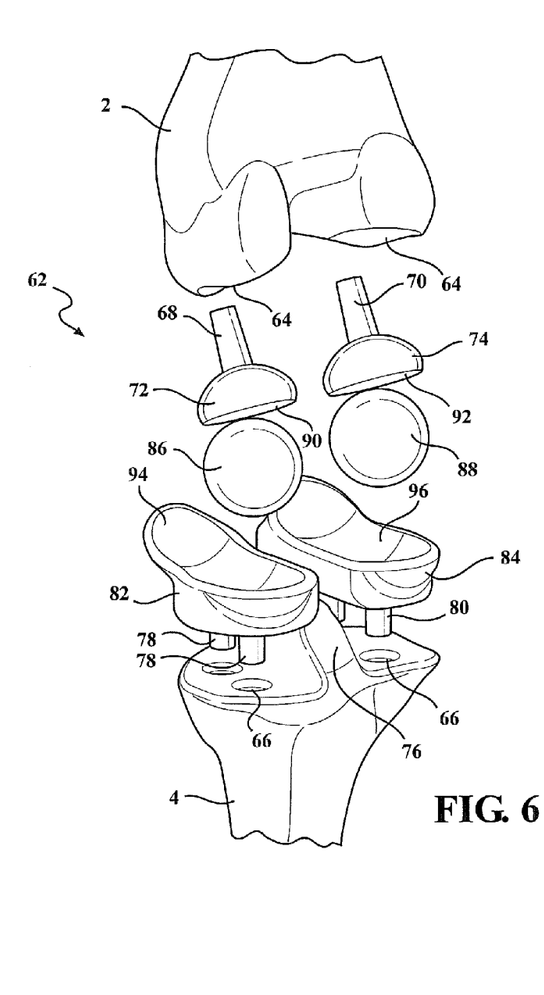
FIG. 6 is an exploded view of the multi-component assembly of FIG. 5 and better illustrating the reconditioned end-configurations established between the upper femur and lower tibia leg bones combined with the pairs of upper bone secured concave seating supports, lower bone secured concave track profiles, and intermediate positioned spherical inter-movable supports.

Proceeding to FIGS. 5-7 in succession, an illustration similar to FIG. 1 is generally depicted at 62 of a knee implant assembly according to a further preferred variant and in which a different set of reconditioned and recess configured profiles within the joint defining end faces of the femur 2 and tibia 4 are defined respectively at 64 and 66 in the exploded view of FIG. 6, respectively and in comparison to the configuration of the corresponding profiles 6 and 8 in FIG. 2. As best depicted in the exploded view of FIG. 6, the upper profiles 64 define reconfigured recesses for receiving inserting posts 68 and 70 associated with upper bone secured concave seating supports 72 and 74, with the lower profiles 66 exhibiting spaced apart pairs of recessed mounting holes separated by a conditioned intermediate projecting bridge 76 (compare to at 9 in FIG. 2) and receiving opposing and underside projecting mounting posts 78 and 80 forming portions of lower bone secured concave track profiles 82 and 84.

Figure 7:
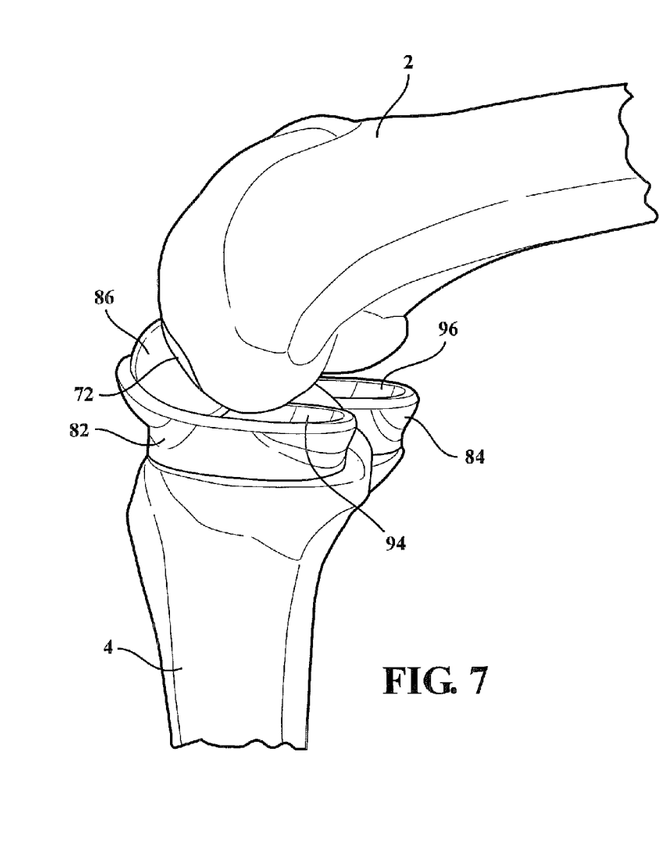
FIG. 7 is an assembled and substantially side rotated perspective similar to FIG. 5 and depicting a substantially 90° bend established between the upper femur and lower tibia with associated combined eccentric rotation and forward lineal displacement of the intermediate spherical supports within the lower bone affixed concave track profiles.

A pair of intermediate positioned spherical inter-movable supports 86 and 88 are provided similar in nature to the corresponding supports 20 and 22 illustrated in FIGS. 1 and 2, and which seat within concave recessed profiles 90 and 92 (see again as best shown in FIG. 6) associated with the upper seating supports 72 and 74 as well as being supported upon inner flared and arcuate extending and upper facing track surfaces 94 and 96 associated with the lower track profiles 82 and 84. FIG. 7 further depicts an assembled and substantially side rotated perspective similar to FIG. 5 and in which a substantially 90° bended position is established between the upper femur 2 and lower tibia 4, with associated combined eccentric rotation and forward lineal displacement of the intermediate spherical supports 86 and 88 better illustrated within the lower bone affixed concave track profiles 94 and 96, such occurring during maintenance of current ligament (meniscus) structure in most applications.

FIG. 8 is largely identical to FIG. 5 and presents only a selected side or ½ implant assembly according to a further potential sub-variant. The significance of FIG. 8 is to illustrate that sub-variants of the joint assembly can be incorporated into reduced of partial reconstructed applications, where applicable, and in situations where an entire reconstructed assembly is either unwarranted or unnecessary. Although not shown, the unreconstructed half of the joint assembly retains its original joint defining structure which, to the extent possible, is unaffected by the reconditioning performed to the implanted half of the joint assembly.

Figure 9:
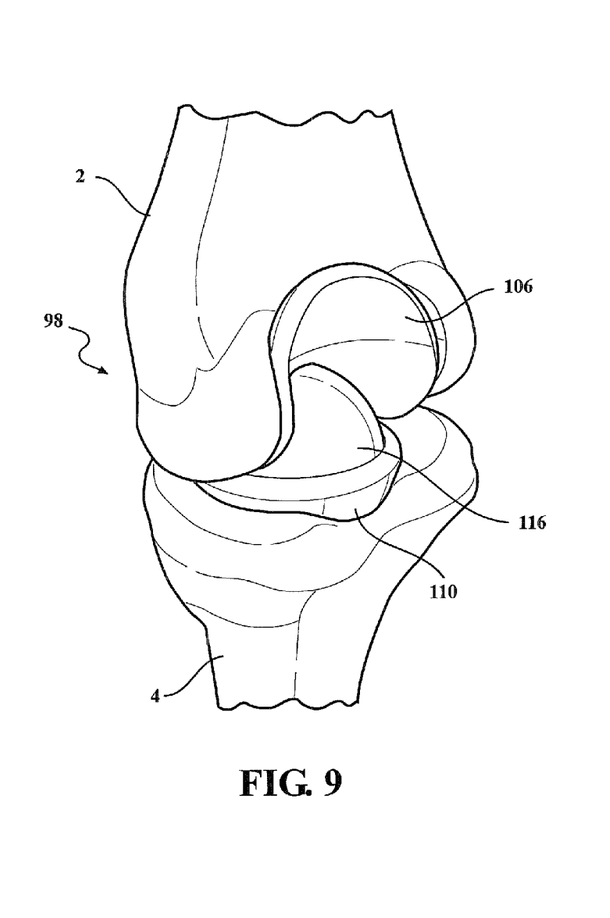
FIG. 9 is an assembled view of a further knee implant assembly and exhibiting a single eccentric and inter-movable interface.
Figure 10:
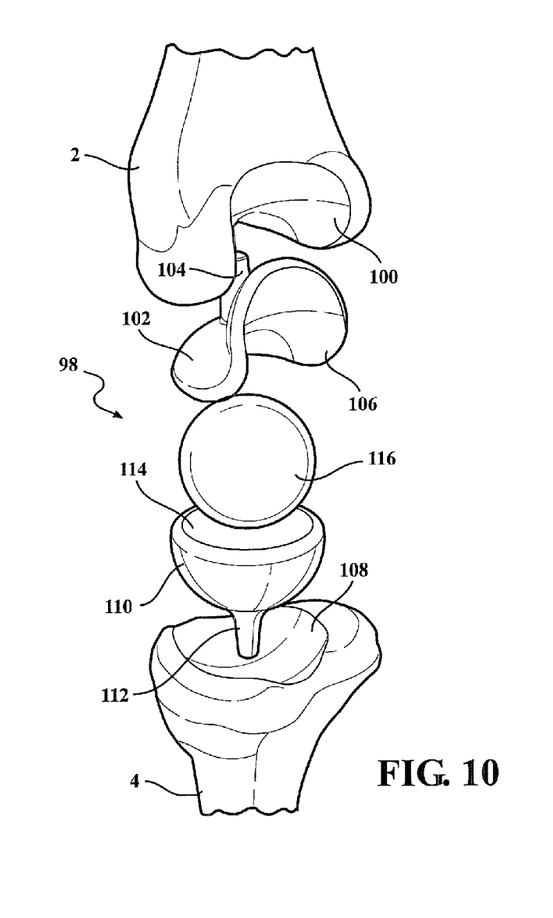
FIG. 10 is an exploded view of the implant assembly of FIG. 9 and better illustrating the reconditioned end-configurations established between the upper femur and lower tibia leg bones including an upper bone secured and inwardly concave flared and pseudo arcuate shaped seating support, a lower bone secured concave support, and an intermediate positioned spherical inter-movable support and which, similar to the previous variants, is eccentrically rotatable at both upper and lower seating locations, combined with linearly/arcuately translatable such as in relation to the upper seating support.

Proceeding on to FIGS. 9 and 10, assembled and exploded views are generally shown at 98 of a further knee implant assembly and exhibiting a single eccentric and inter-movable interface. Specifically, and as best depicted in FIG. 10, a reconditioned end-configuration 100 established within the upper femur 2 receives (such as again in a cemented or other permanently affixing fashion) an inwardly concave flared and pseudo arcuate shaped seating support 102 (as best shown in FIG. 10) which further exhibits a reverse face/inwardly projecting support post 104 anchoring into an aligning recess machined into the upper femur 2 (not shown), combined with the arcuate end surface profile 100 of the bone 2 mirroring the undulating pattern of the reverse/back surface of the arcuate support 102. A corresponding outer facing surface 106 of the upper support 102 exhibits an inwardly flared and slightly elongated profile not dissimilar to a reverse saddle (or potato chip) shape.

A lower reconditioned surface profile, see at 108, is configured within the joint defining end face of the tibia bone 4 and anchors a lower bone secured concave support 110 further exhibiting a lower extending mounting stem or post 112 received within a corresponding mating recess (not shown) associated with an innermost machined location of the lower profile 108. The lower concave support 110 further exhibits an outwardly facing and substantially hemi-spherical bowl shape 114.

A single and intermediate positioned spherical inter-movable support 116 and which, similar to the previous variants, is eccentrically rotatable at both upper and lower seating locations, combined with linearly/arcuately translatable such as in relation to the inner elongated surface 106 of the upper seating support 102, while exhibiting both eccentric rotation as well as a limited degree of lateral or fore to aft adjustability within the seating pocket defined by the hemi-spherical bowl shape 114 within the lower anchored support 110. It is further envisioned that the respective materials of the upper 102 and lower 110 supports can exhibit either the same or different properties which render them respectively harder or softer and this, combined with the material properties of the intermediate positioned spherical support 116 again assists in establishing varying dynamic operating properties.

Figure 11:
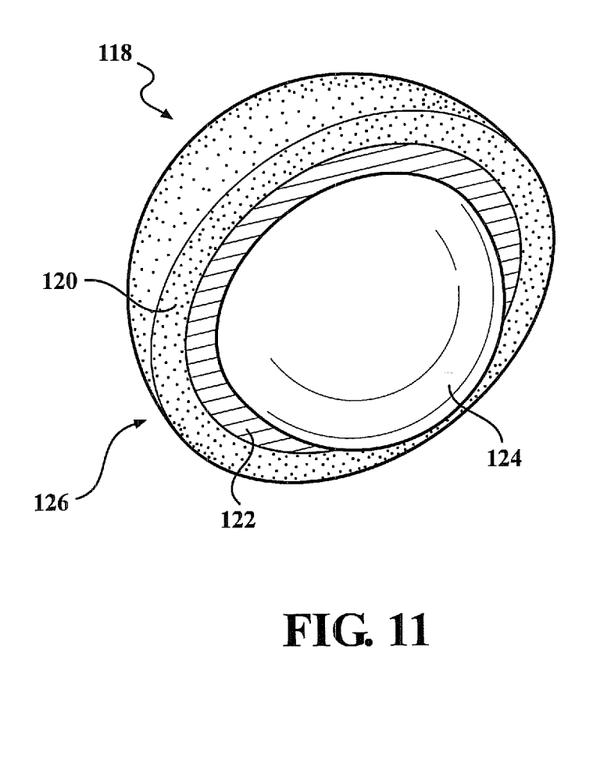
FIG. 11 is an illustration of a spherical support associated with such as the variant of FIGS. 9 and 10 and presented similarly to that previously depicted in FIG. 4 with a smooth faced and hard innermost portion exhibited in three dimension perspective and in eccentric rotatable fashion relative to an intermediate harder material in turn encased within a softest outermost material.
Figure 12:
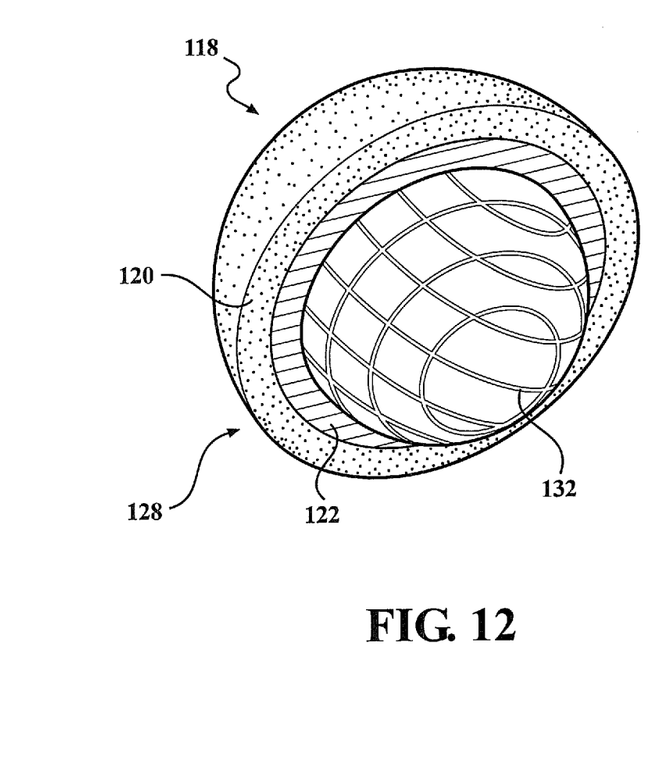
FIG. 12 is an illustration largely identical to FIG. 11 of an alternately configured spherical support with lubricating grooves illustrated along an exterior spherical profile of the innermost hardened material.

FIG. 11 is an illustration in cutaway, generally at 118, of a single spherical support associated with such as the variant of FIGS. 9 and 10, and presented similarly to that previously depicted in FIG. 4. The single support 118 includes a softest (cushioning) outermost layer 120, a harder intermediate layer 122 and a smooth faced and similarly hard innermost spherical body defined by an outer surface 124 and which, similar to FIG. 4, is exhibited in three dimension perspective and in eccentric rotatable fashion about an interface 126 established relative to the inner surface of the intermediate harder material layer 122. FIG. 12 is an illustration largely identical to FIG. 11 of an alternately configured spherical support, see at 128, and exhibiting a network of lubricating grooves 130 illustrated along an exterior spherical profile of an innermost hardened material 132, with corresponding outermost softest 120 and intermediate harder 122 material layers again provided as previously described.

Figure 13:
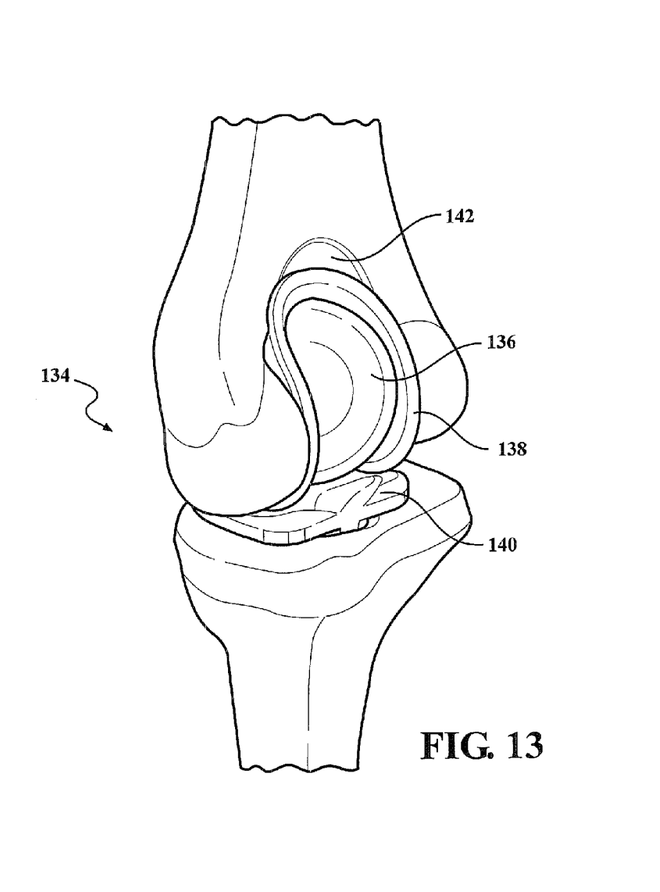
FIG. 13 is an assembled view of a still further knee implant assembly analogous to that depicted in FIG. 9 and depicting an alternately configured single eccentric and inter-movable interface.
Figure 14:
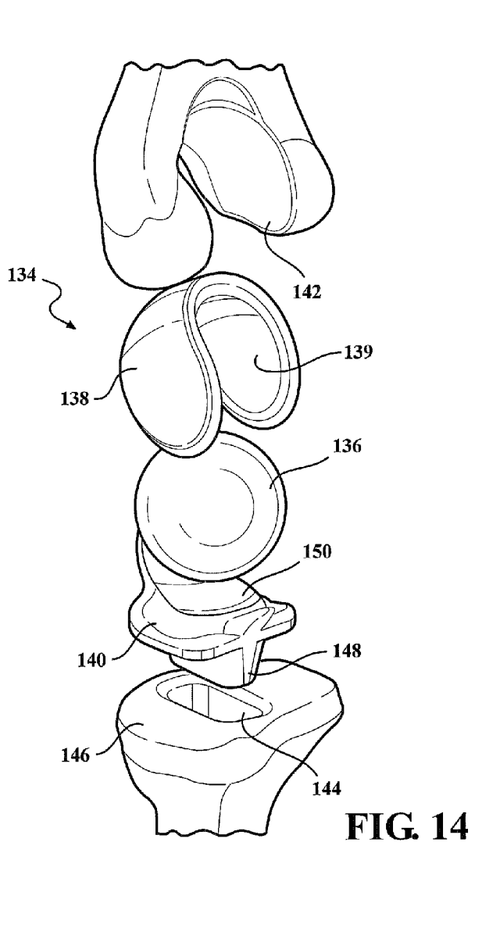
FIG. 14 is an exploded view of the implant assembly of FIG. 13 and better illustrating the reconditioned end-configurations established between the upper femur and lower tibia leg bones including an upper bone recess secured pocket, a lower bone secured arcuate/concave support, and an intermediate positioned spherical inter-movable support and which, similar to the previous variants, establishes a limited eccentrically rotatable configuration with the upper leg receiving pocket, combined with a further measure of eccentric support with the lower leg secured arcuate/concave support and again combined with a limited degree of linearly/arcuately translatable motion along the lower leg secured arcuate support pathway.

FIGS. 13 and 14 depict, generally at 134, assembled and exploded views of a still further knee implant assembly analogous to that depicted in FIG. 9 and depicting an alternately configured single eccentric and inter-movable interface defined between a single spherical and intermediate component 136 and respective upper 138 and lower 140 bone end secured components.

As further depicted in FIG. 14, an upper reconditioned end-configuration is illustrated at 142 established within the end of the upper femur 2 and exhibits an enlarged spherical surface receiving pocket established between lowermost projection locations of the femur. The upper component 138 is dimensioned to be anchor mounted within the recess profile 142, the upper component 138 exhibiting a like spherical receiving and flared inner pocket 139 established between a pair of arcuate edged ears or lobes collectively defining the upper component 138. As shown in FIG. 13 this in turn eccentrically seats therebetween a majority of the spherical component 136 as shown in FIG. 13.

Figure 15:
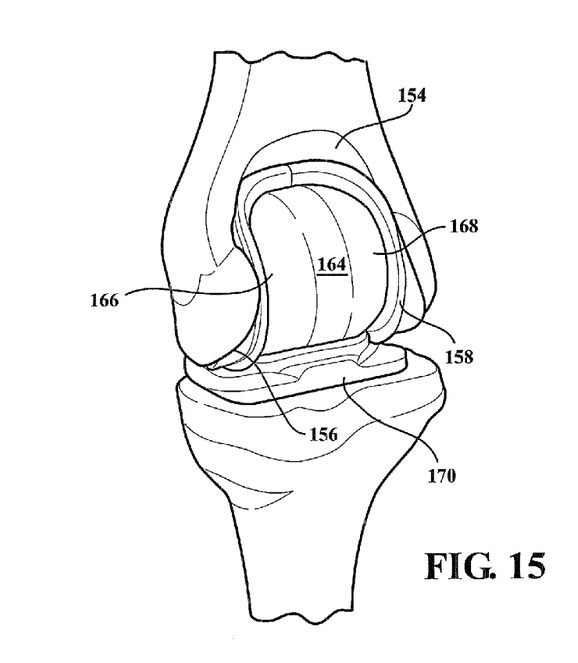
FIG. 15 is a perspective assembled illustration similar to that depicted in FIG. 14 and in which the upper bone recess secured pocket component and intermediate support are both reconfigured to accommodate a substantially intermediate flattened and pseudo roller/egg shaped support according to a yet further preferred variant.
Figure 16:
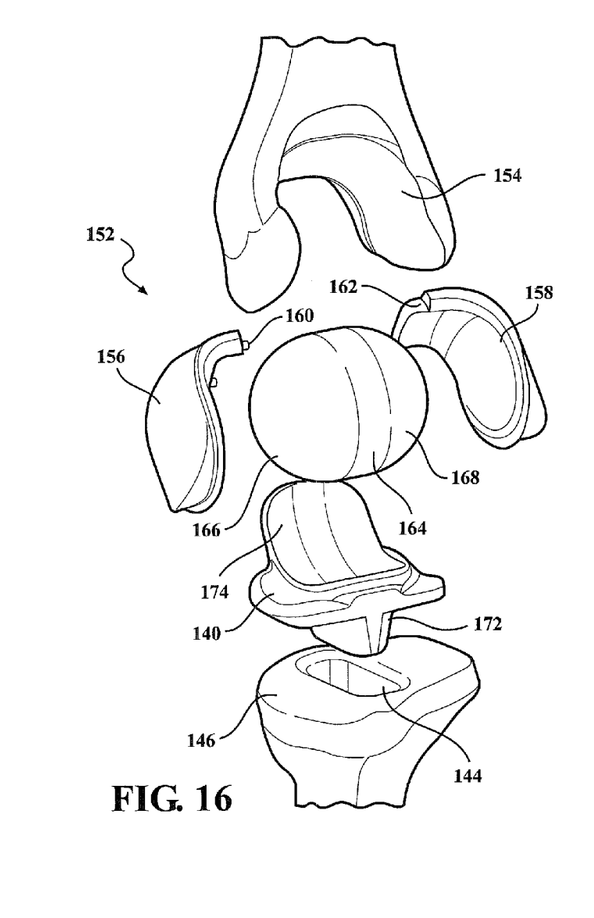
FIG. 16 is an exploded view of the implant assembly of FIG. 15 and better illustrating the reconditioned end-configurations established between the upper femur and lower tibia leg bones including first and second assembled and recess mounted components defining the upper bone recess secured pocket, a lower bone secured arcuate/concave support, and an intermediate positioned inter-movable support exhibiting the pseudo spherical/cylindrical flattened and elongated profile for establishing a more robust upper rotational support combined with like lower rotational support and limited arcuate/linear displacement.

As shown in FIG. 14, the lower tibia leg bone includes an upper bone recess secured pocket 144 (establishing a generally rectangular shaped profile surrounded by a generally flattened lip edge 146) for receiving the lower bone secured arcuate/concave support 140. The lower anchoring component 140 exhibits a bottom mounting pedestal or base 148 for seating within the recessed pocket 144 of the tibia bone end face, the component further exhibiting and opposite/upwardly facing and inwardly flared/arcuate track support 150. In this fashion, the intermediate positioned spherical inter-movable support 136 establishes a limited eccentrically rotatable configuration with the upper leg receiving pocket, combined with a further measure of eccentric support with the lower leg secured arcuate/concave support and again combined with a limited degree of linearly/arcuately translatable motion along the lower leg secured arcuate support pathway;

Referring finally to FIGS. 15 and 16, respective perspective assembled and exploded illustrations similar to that depicted in FIG. 14 are generally shown at 152 of a modified sub-variant of FIG. 13 and in which an upper femur bone recess configuration 154 exhibits an enlarged/widened inner profile in comparison to that previously shown at 142, with the lower tibia bone recess configuration again be substantially as depicted at 144 and 146. The upper anchoring component is depicted as a pair of arcuate/ear shaped an assembleable components 156 and 158 (see further upper end assembling tabs 160 and slots 162 established between the components 156 and 158).

The ear shaped components 156 and 158 are pre-assembled about a widened and pseudo roller/egg shaped support exhibiting a cylindrically flattened central location 164 with opposite spherical end profiles 166 and 168 (see again as best shown in FIG. 16), following which the subassembly is installed within the upper recess configuration 142 as depicted in FIG. 15. A lower anchoring component 170 (similar in respects to that previously described at 140 in FIG. 14) exhibits a bottom mounting pedestal or base 172 for seating within the recessed pocket 144 of the tibia bone end face, the component further exhibiting and opposite/upwardly facing and inwardly flared/arcuate track support 174, which is in turn widened in comparison to that previously referenced at 150 for the purpose of supporting the correspondingly widened surface profile of the modified pseudo cylindrical/spherical end shaped intermediate support 164. The construction 152 therefore provides a further non-limiting example of a more robust joint support assembly of a type contemplated by the present invention.

Having described my invention, other and additional preferred embodiments will become apparent to those skilled in the art to which it pertains, and without deviating from the scope of the appended claims.

We claim:

1. A multi-component joint assembly incorporated into reconditioned end surfaces established between an upper bone and an opposing lower bone, said assembly comprising:
   a first component adapted to being anchored into the upper reconditioned bone end surface and exhibiting a first exposed support surface;
   a second component adapted to being anchored into the lower reconditioned bone end surface and exhibiting a second exposed support surface; and
   a spherical shaped component supported in rotational and linear/arcuate translatable fashion between said first and second anchored components, said spherical shaped component further having a multi-layer composition including a softer outer layer and first and second harder interior layers establishing a rotational interface therebetween.

2. The joint assembly as described in claim 1, at least one of said components further exhibiting a hemispherical recess for substantially seating said spherical shaped component.

3. The joint assembly as described in claim 1, each of said first, second and spherical shaped components further being constructed of at least one of a metal, plastic, polymer or composite material.

4. The joint assembly as described in claim 1, further comprising a grid pattern of lubricating grooves defined in a surface of an innermost spherical shaped portion of said spherical component facilitating said rotational interface.

5. A multi-component joint assembly incorporated into reconditioned end surfaces established between an upper bone and an opposing lower bone, said assembly comprising:

a first component configured to be anchored into the upper reconditioned bone end surface and exhibiting a first exposed support surface having an inwardly flared and elongated profile;

a second component configured to be anchored into the lower reconditioned bone end surface and exhibiting a second hemispherical recess shaped support surface; and a spherical shaped component supported in rotational contact with each of said first and second components, said spherical shaped component also supported in linear/arcuate translatable fashion along said inwardly flared and elongated profile of said first anchored component, said spherical shaped component having a multi-layer composition including a softer outer layer and at least one harder interior layer, said outer and interior layers establishing a rotational interface therebetween.

\* \* \* \* \*